(12) United States Patent
Nakamura et al.

(10) Patent No.: US 8,757,876 B2
(45) Date of Patent: Jun. 24, 2014

(54) X-RAY APPARATUS

(75) Inventors: Toshiaki Nakamura, Nagaokakyo (JP); Hiroshi Inoue, Kyoto (JP); Koji Yoshida, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 13/516,930

(22) PCT Filed: Dec. 18, 2009

(86) PCT No.: PCT/JP2009/007013
§ 371 (c)(1),
(2), (4) Date: Jun. 18, 2012

(87) PCT Pub. No.: WO2011/074047
PCT Pub. Date: Jun. 23, 2011

(65) Prior Publication Data
US 2012/0257724 A1    Oct. 11, 2012

(51) Int. Cl.
*A61B 6/04* (2006.01)
(52) U.S. Cl.
USPC .............................................. 378/189; 378/62
(58) Field of Classification Search
CPC .................................................... A61B 6/0414
USPC ........................................................ 378/189
See application file for complete search history.

(56) References Cited

U.S. PATENT DOCUMENTS

| 6,027,247 | A | 2/2000 | Tachi et al. |
| 2003/0174806 | A1* | 9/2003 | Francke et al. ................. 378/37 |
| 2006/0078084 | A1* | 4/2006 | Souchay et al. ................ 378/21 |
| 2010/0296626 | A1 | 11/2010 | Hibino et al. |

FOREIGN PATENT DOCUMENTS

| CN | 1582855 A | 2/2005 |
| CN | 101547646 A | 9/2009 |
| JP | 8-275936 | 10/1996 |
| JP | 8-275939 | 10/1996 |
| JP | 8-275941 | 10/1996 |
| JP | 2004-160263 | 6/2004 |
| JP | 2005-000353 | 1/2005 |

OTHER PUBLICATIONS

International Search Report issued in International Patent Application No. PCT/JP2011/000567 dated May 17, 2011.

* cited by examiner

*Primary Examiner* — Hoon Song
*Assistant Examiner* — Dani Fox
(74) *Attorney, Agent, or Firm* — McDermott Will & Emery LLP (57) ABSTRACT

An X-ray apparatus in this example of the invention includes a compression unit that enables to move independently of an X-ray tube supporting device and an X-ray detector for compressing a region of interest of a subject; and a connecting part for connecting the X-ray detector to the compression unit and disconnecting the X-ray detector from the compression unit. Consequently, when the compression unit is not used, the compression unit is located in a retracted position. Thus a space can be secured around the subject placed on a top board. On the other hand, when the compression unit is used, the connecting part connects the X-ray detector to the compression unit. Thereby a compression member of the compression unit can always press a site of interest of the subject at the center of a detecting surface of the X-ray detector.

16 Claims, 7 Drawing Sheets

X-RAY APPARATUS

RELATED APPLICATIONS

This application is the U.S. National Phase under 35 U.S.C. §371 of International Application No. PCT/JP2009/007013, filed on Dec. 18, 2009, the disclosure of which Application is incorporated by reference herein.

TECHNICAL FIELD

This invention relates to an X-ray apparatus provided with a compression unit for compressing a region of interest of a subject.

BACKGROUND ART

A conventional X-ray apparatus includes a top board for supporting a subject placed thereon, an X-ray tube for irradiating the subject with X-rays, an X-ray detector, such as a flat panel X-ray detector (FPD), facing the X-ray tube across the top board of a radiographing table for detecting X-rays transmitting through the subject. At least one of the X-ray tube and the X-ray detector is supported on a strut. The strut has a compression unit supported thereon for compressing a site of interest of the subject.

The compression unit includes a compression member for compressing the subject and a compression-unit movement drive. The movement drive moves the compression member in a direction of compressing the subject and in a direction opposite thereto. The subject having taken a barium contrast media is placed on the top board. Then radiography is conducted while the compression unit compresses the site of interest of the subject placed on the top board. See, for example, Patent Literature 1.

The following are disclosed as for an X-ray apparatus provided with a compression unit. See, for example, Patent Literatures 2 through 5. Specifically, an X-ray apparatus includes a radiographing table having a top board for supporting a subject placed thereon, an X-ray irradiation apparatus suspended from a ceiling, and an X-ray imaging device below the radiographing table for taking an X-ray image. The radiographing table of the X-ray apparatus has rails on both side faces thereof for attaching accessories. A compression unit is attached to the rails.

[Patent Literature 1] Japanese Patent Publication No. 2005-353A
[Patent Literature 2] Japanese Patent Publication No. H08-275936A
[Patent Literature 3] Japanese Patent Publication No. H08-275939A
[Patent Literature 4] Japanese Patent Publication No. H08-275941A
[Patent Literature 5] Japanese Patent Publication No. 2004-160263A

DISCLOSURE OF THE INVENTION

Summary of the Invention

The X-ray apparatus as above performs physical examinations, such as a stomach and intestines of a subject, using a compression unit. In addition to this, such X-ray apparatus conducts radiography, such as inspections using an endoscope while radiographing, with no use of a compression unit. In this case, devices such as a monitor of an endoscope and an electrocardiogram are placed around the subject placed on the top board of the radiographing table, or an operator has access to the subject. Thus, a space is needed accordingly. On the other hand, the strut for supporting the compression unit is arranged around the subject placed on the top board. As a result, a problem may arise that access to the subject on the top board is restricted. For instance, when the strut is connected to an X-ray detector, the strut is moved as the detector moves. This may lead to further restriction in access to the subject on the top board.

Moreover, the compression unit is attached to the rails. Consequently, the devices described in the latter part of the foregoing paragraph are movable independently of an X-ray irradiation apparatus and an X-ray imaging device. On the other hand, the devices have to be aligned independently of the X-ray irradiation apparatus and the X-ray imaging device in use of the compression unit.

This invention has been made regarding the state of the art noted above, and its object is to provide an X-ray apparatus that enables to secure a space around a subject placed on a top board when a compression unit is not used, and enables to operate a compression unit with ease when the compression unit is used.

Means for Solving the Problem

This invention is constituted as stated below to achieve the above object. An example of the invention is an X-ray apparatus including an X-ray tube supporting device with an X-ray tube for applying X-rays; a radiographing table with a top board for supporting a subject placed thereon and an X-ray detector facing the X-ray tube across the top board for detecting X-rays transmitting through the subject; a compression unit that enables to move independently of the X-ray tube supporting device and the X-ray detector for compressing a site of interest of the subject; and a connecting part for connecting the X-ray detector to the compression unit and disconnecting the X-ray detector from the compression unit.

The X-ray apparatus in this example of the invention includes the compression unit that enables to move independently of the X-ray tube supporting device and the X-ray detector for compressing a site of interest of the subject; and the connecting part for connecting the X-ray detector to the compression unit and disconnecting the X-ray detector from the compression unit. Consequently, when the compression unit is not used, the compression unit is disconnected from the X-ray detector. Thereby the X-ray detector can be located in a radiographing position, whereas the compression unit can be located in a retracted position out of an operator's way. As a result, a space is generated around the subject placed on the top board of the radiographing table, which achieves access to the subject or arrangement of devices. On the other hand, when the compression unit is used, the connection part connects the X-ray detector to the compression unit. Thereby the center of a detecting surface of the X-ray detector can conform to the center of a compression member of the compression unit for compressing the subject. As a result, compressing can always be performed at the center of the detecting surface of the X-ray detector, which enables to operate the compression unit with no difficulty.

Moreover, the radiographing table of the X-ray apparatus in this example of the invention preferably includes an X-ray detector movement drive for driving the X-ray detector as to move in a plane parallel to a surface of the top board on which the subject is placed. The X-ray detector can be moved by the X-ray detector movement drive in a plane parallel to the surface of the top board on which the subject is placed. Thereby the X-ray detector movement drive can move the X-ray detector freely. In addition, the X-ray detector movement drive can move integrally with the X-ray detector and the compression unit connected via the connection part. That is, the X-ray detector movement drive can move the compression unit. Consequently, the compression unit can be moved to its retracted position by the X-ray detector movement drive without an actuator for moving the compression unit, which achieves a simple configuration and reduced manufacturing costs.

Moreover, it is preferable that the compression unit of the X-ray apparatus in this example of the invention is movably supported on the radiographing table. Thereby the compression unit can be inclined or be moved upward and downward integrally with the compression unit. For instance, if rails with the compression unit provided thereon are placed on a floor, the compression unit can be adopted with the top board of the radiographing table being in a horizontal state and the top board in a given level, whereas the compression unit is not possibly adopted when the radiographing table is inclined or moved upward and downward. In addition, the compression unit that moves along with inclination or vertical movement of the radiographing table leads to higher manufacturing costs.

Moreover, the X-ray tube supporting device of the X-ray apparatus in this example of the invention is preferably of ceiling-suspended travelling type. Thereby the X-ray tube can be suspended from the ceiling. As a result, a space can be made additionally around the subject placed on the top board of the radiographing table.

Moreover, the X-ray apparatus in this example of the invention preferably includes a compression-unit movement drive for driving the compression unit as to move in a plane parallel to a surface of the top board on which the subject is placed. Thereby the compression unit can move independently of the X-ray detector in the plane parallel to a surface of the top board on which the subject is placed. For instance, when the compression unit is used, the compression-unit movement drive moves the compression unit into a radiographing position, and can connect the X-ray detector to the compression unit via the connection part. On the other hand, when the compression unit is not used, the connection part disconnects the X-ray detector from the compression unit, whereby the X-ray detector can be moved into a given radiographing position and the compression unit can be moved into a retracted position. Consequently, the X-ray detector and the compression unit can be operated with enhanced efficiency.

Effect of the Invention

According to the X-ray apparatus in the example of the invention, when the compression unit is not used, the connection part disconnects the X-ray detector from the compression unit, whereby the X-ray detector is located in a radiographing position and the compression unit is located in the retracted position out of an operator's way. As a result, a space is generated around the subject placed on the top board of the radiographing table, which achieves access to the subject or arrangement of devices in the space. On the other hand, when the compression unit is used, the connection part connects the X-ray detector to the compression unit. Thereby compressing can always be made at the center of a detecting surface of the X-ray detector, which achieves easy operation of the compression unit.

DESCRIPTION OF REFERENCES

1 . . . X-ray tube supporting device
2 . . . radiographing table
3 . . . compression unit
5 . . . X-ray tube
21 . . . top board
21a . . . surface of a top board on which a subject M is placed
23 . . . flat panel X-ray detector (FPD)
25 . . . X-ray detector supporting mechanism
27 . . . X-ray detector movement drive
59 . . . compression member
77 . . . compression-unit supporting mechanism
93 . . . connecting part
121 . . . compression-unit movement drive
M . . . subject

BEST MODE FOR CARRYING OUT THE INVENTION

Example 1

Figure 1:
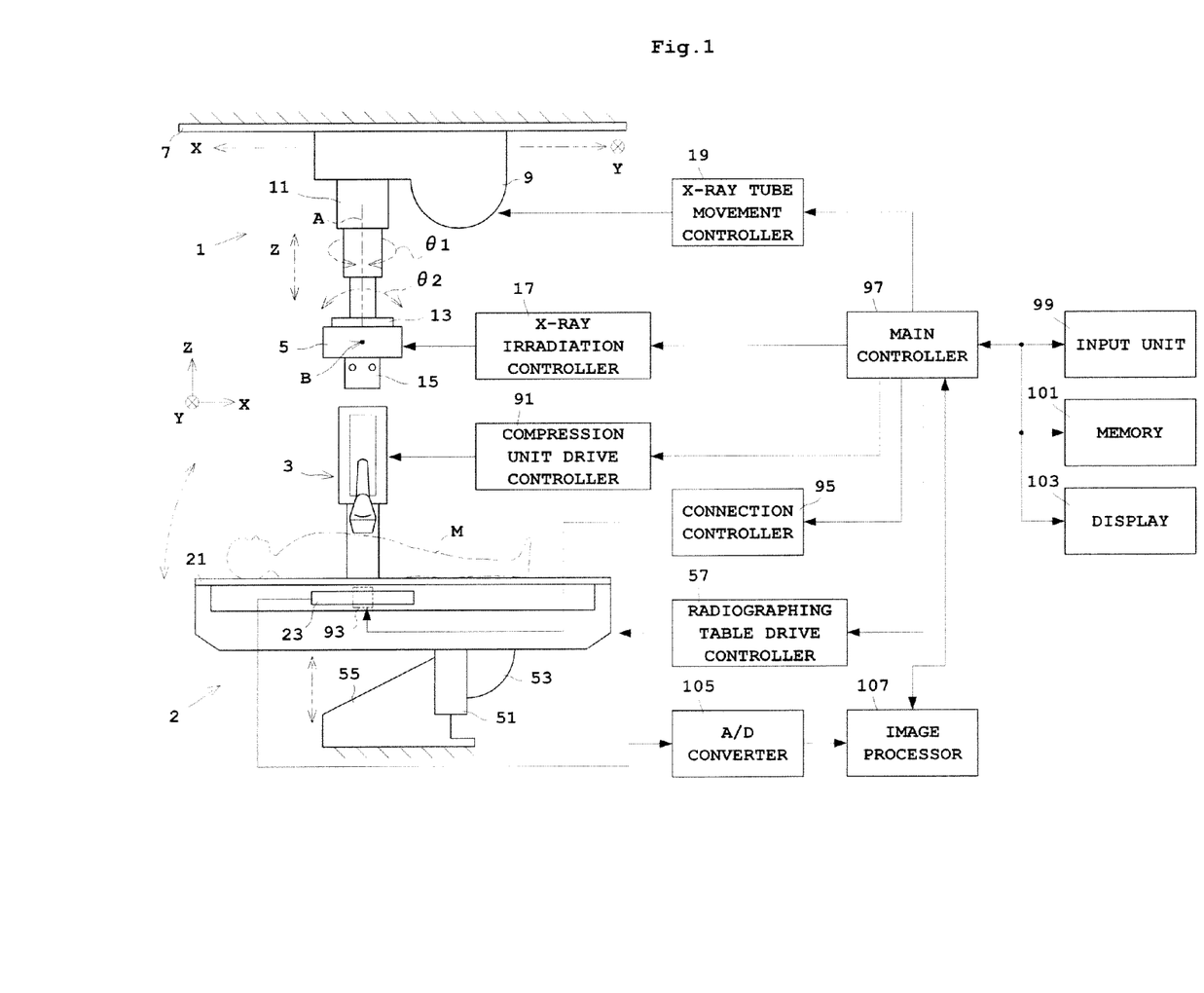
FIG. 1 is a schematic view of an X-ray apparatus according to an example.
Figure 2:
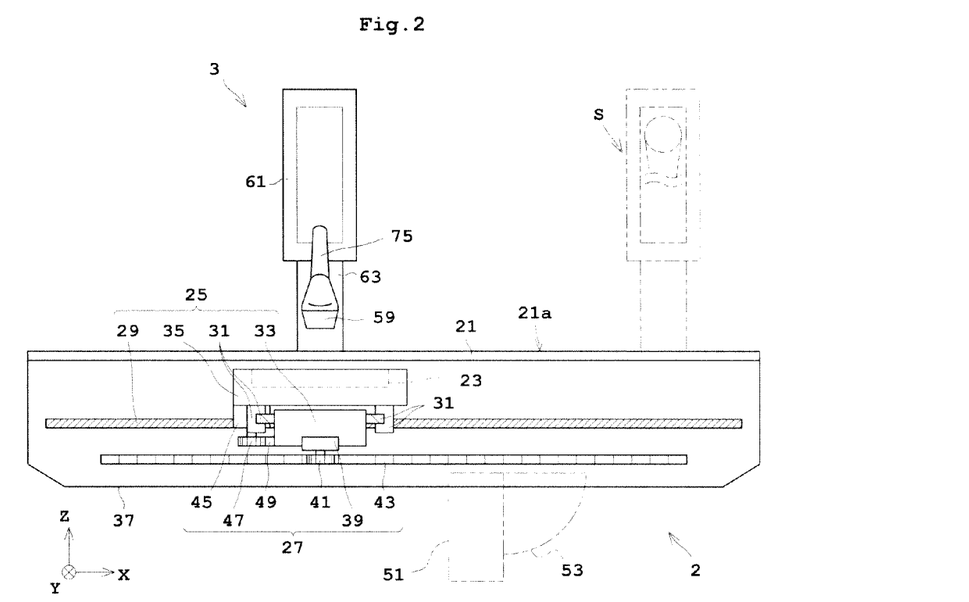
FIG. 2 is a schematic front view of a compression unit and a radiographing table of the X-ray apparatus according to the example.
Figure 3:
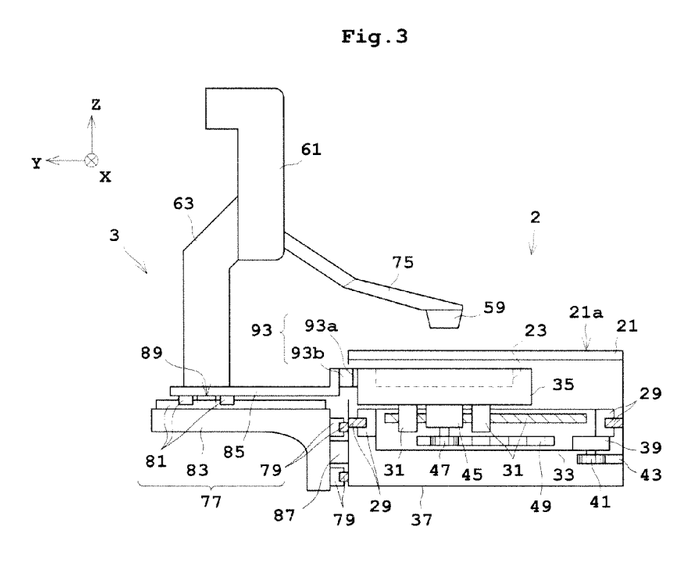
FIG. 3 is a schematic left side view of the compression unit and the radiographing table of the X-ray apparatus according to the example.
Figure 4:
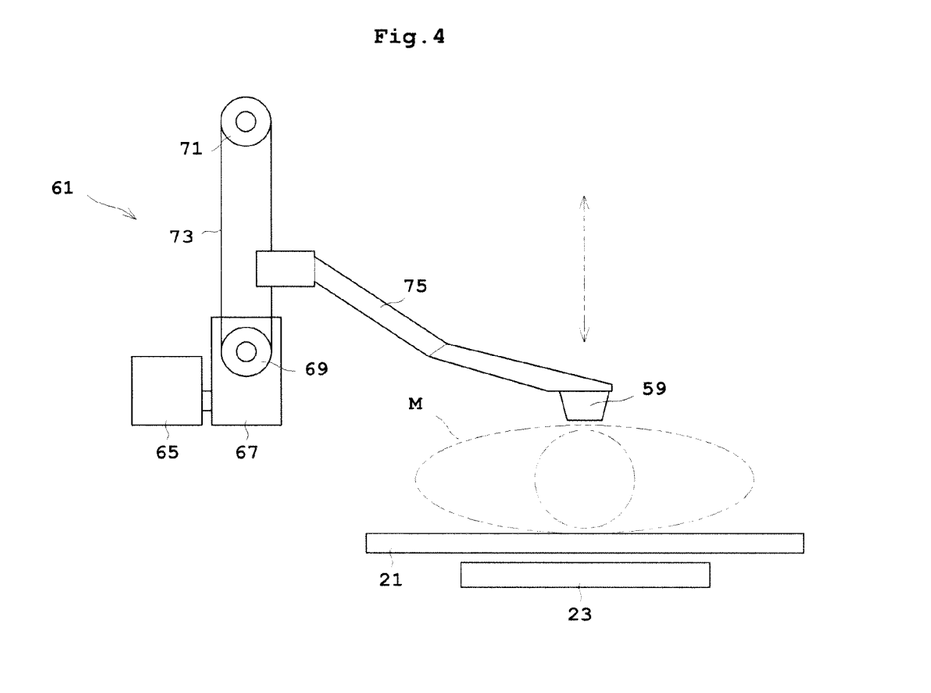
FIG. 4 is a schematic view of a compression-unit movement drive for the compression unit of the X-ray apparatus according to the example.
Figure 5:
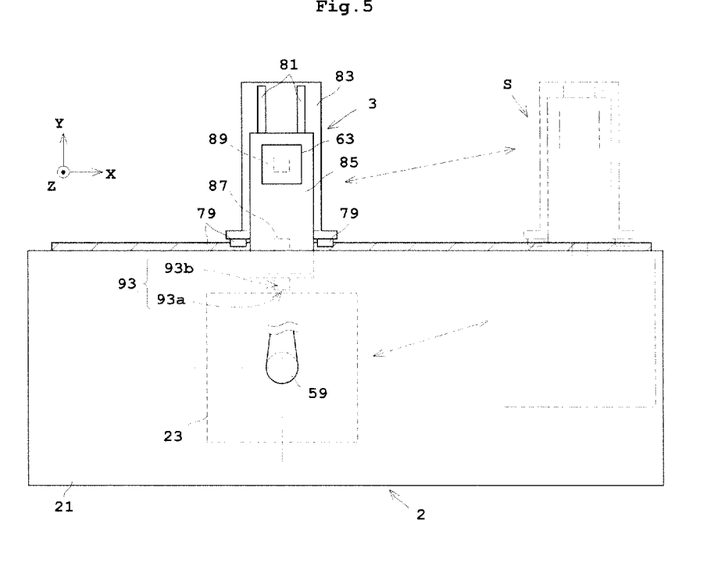
FIG. 5 is a schematic plan view of the compression unit and the radiographing table of the X-ray apparatus according to the example.

Example 1 of the invention will be described hereinafter with reference to the drawings. FIG. 1 is a schematic view of an X-ray apparatus. FIG. 2 is a schematic front view of a compression unit and a radiographing table of the X-ray apparatus. FIG. 3 is a schematic left side view of the compression unit and the radiographing table of the X-ray apparatus. FIG. 4 is a schematic view of a compression-unit movement drive for the compression unit of the X-ray apparatus. FIG. 5 is a schematic plan view of the compression unit and the radiographing table of the X-ray apparatus according to the example.

Reference is now made to FIG. 1. The X-ray apparatus is provided with an X-ray supporting device 1 for irradiating a subject M with X-rays, a radiographing table 2 for supporting the subject M placed thereon, and a compression unit 3 for compressing a site of interest of the subject M.

<X-ray Tube Supporting Device>

Examples of the X-ray tube supporting device 1 includes a type of suspending an X-ray tube 5 for applying X-rays from a ceiling and a type of supporting an X-ray tube 5 on a floor.

In this example, an X-ray tube supporting device of a ceiling-suspended travelling type with the X-ray tube 5 suspended from the ceiling (hereinafter, appropriately abbreviated as an "X-ray supporting device") is to be described as one example of the X-ray tube supporting device 1.

The X-ray tube supporting device 1 has rails 7 arranged on the ceiling and a carriage part 9 that can move along the rails 7. An extendable strut 11 that can extend upward and downward freely is provided on a lower portion of the carriage part 9. The X-ray tube 5 is provided via an attachment block 13 on an opposite side of the extendable strut 11 connected to the carriage part 9. The X-ray tube 5 includes an irradiation hole where a collimator 15 for controlling irradiation fields of X-rays to be applied is attached.

The rails 7 are placed perpendicular to a transverse direction (an X-direction) and a plane direction of figures (a Y-direction). So, the carriage part 9, the extendable strut 11, the attachment block 13, and X-ray tube 5 are movable integrally in a horizontal plane (the XY-directions). Moreover, the extendable strut 11 extends upward and downward. As a result, the attachment block 13 and X-ray tube 5 can be moved integrally in an up-and-down direction (a Z-direction). The X-ray tube 5 can turn around θ1 about an axial center A of the strut parallel to a vertical direction and around θ2 about an axial center B of the strut parallel to the plane direction (the Y-direction). That is, the X-ray tube 5 can move in the horizontal plane (XY-directions) and the up-and-down direction (Z-direction), and can turn around θ1 about the axial center A and around θ2 about the axial center B.

The X-ray tube 5 irradiates the subject M with X-rays through control by an X-ray irradiation controller 17 with a high voltage power supply (not shown). The X-ray irradiation controller 17 performs control of X-ray irradiation required for the X-ray tube 5 in accordance with irradiation conditions, such as a tube voltage and a tube current, that are set in advance by an input unit (99) etc., to be mentioned later. Moreover, an X-ray tube movement controller 19 controls movement of the X-ray tube 5 in the horizontal plane (the XY-directions) and in the up-and-down direction (the Z-direction) as well as turns of the X-ray tube 5 around è1 about the axial center A and around è2 about the axial center B. Here, such actuator as a motor, a pinion, and a rack, not shown, moves or turns the X-ray tube 5.

<Radiographing Table>

Next, referring is made to FIGS. 2 and 3. Here, the radiographing table 2 and the compression unit 3 mentioned later are described using the X-, Y-, and Z-directions under a state where the surface of a top board 21 on which the subject M is placed is horizontal.

The radiographing table 2 is provided with a top board 21 for supporting a subject M placed thereon, and a flat panel X-ray detector (hereinafter, appropriately abbreviated as an "FPD") 23 that faces the X-ray tube 5 of the X-ray tube supporting device 1 across the top board 21 for detecting X-rays transmitting through the subject M. Here, the FPD 23 corresponds to the X-ray detector in the example of the invention.

Moreover, the radiographing table 2 includes an X-ray detector supporting mechanism 25 for supporting the FPD 23 so as to move in a plane parallel to a surface 21a of the top board 21 on which the subject M is placed, and an X-ray detector movement drive 27 for driving the FPD 23 that is supported so as to move in a plane parallel to the surface 21a of the top board 21 on which the subject M is placed.

The X-ray detector supporting mechanism 25 includes a first slide rail 29, a second slide rail 31, a first support block 33, and a second support block 35. Moreover, the X-ray detector supporting mechanism 25 is supported on a main frame 37 of the radiographing table 2.

Specifically, the first slide rail 29 is provided on the main frame 37 of the radiographing table 2 in parallel with a longitudinal direction of the top board 21 (the X-direction). The first support block 33 is supported as to move along the first slide rail 29. The second slide rail 31 is provided on the first support block 33 in parallel with a transverse direction of the top board 21 (the Y-direction). The second support block 35 is supported as to move along the second slide rail 31. The FPD 23 is supported on the X-ray detector support block 33. Consequently, the FPD 23 is supported as to move freely in a plane parallel to the surface 21a of the top board 21.

The X-ray detector movement drive 27 drives the FPD 23 movably supported on the main frame 37 of the radiographing table 2 by the X-ray detector supporting mechanism 25 as to move into a given position in a plane parallel to the surface 21a of the top board 21. The X-ray detector movement drive 27 includes a first motor 39, a first pinion 41, and a first rack 43 for driving the FPD 23 as to move in the longitudinal direction of the surface 21a of the top board 21. The X-ray detector actuator 27 also includes a second motor 45, a second pinion 47, and a second rack 49 for driving the FPD 23 as to move in the transverse direction of the surface 21a of the top board 21. The X-ray detector movement drive 27 is provided with a rotary encoder, not shown, as a position detection sensor, for example.

The first rack 43 is fixed on the main frame 37 parallel to the longitudinal direction of the top board 21 (the X-direction). The first pinion 41 is attached to an output shaft of the first motor 39. The first motor 39 is attached to the first support block 33 such that teeth of the first rack 43 engage with teeth of the first pinion 41. Thereby, the first support block 33, i.e., the FPD 23, can move in the longitudinal direction of the surface 21a of the top board 21.

Moreover, the second rack 49 is fixed on the first support block 33 in parallel with the transverse direction of the top board 21 (the Y-direction). The second pinion 47 is attached to an output shaft of the second motor 45. The second motor 45 is attached to the second support block 35 such that teeth of the second rack 49 engage with teeth of the second pinion 47. Thereby, the second support block 35, i.e., the FPD 23, can move in the transverse direction of the surface 21a of the top board 21.

As shown in FIGS. 1 and 2, the radiographing table 2 includes a top-board lifting section 51, a rise and fall section 53, and a base 55. The top-board lifting section 51 moves the subject M placed on the top board 21 upward and downward through moving the top board 21, the FPD 23, the X-ray detector supporting mechanism 25, the X-ray detector movement drive 27, and the main frame 37 integrally upward and downward. The rise and fall section 53 inclines the subject M placed on the top board 21 through inclining the top board 21, the FPD 23, the X-ray detector supporting mechanism 25, the X-ray detector movement drive 27, and the main frame 37 integrally. The base 55 is fixed on a floor. The top-board lifting section 51 and the rise and fall section 53 are attached to the lower portion of the main frame 37. The main frame 37 is supported on the base 55 fixed on the floor, via the top-board lifting section 51.

A radiographing table drive controller 57 performs control to drive the FPD 23, the X-ray detector movement drive 27, the top-board lifting section 51, and the rise and fall section 53.

<Compression Unit and Compression-Unit Supporting Mechanism>

As shown in FIGS. 2 and 3, the compression unit 3 includes a compression member 59 for compressing the subject M, a compression-unit movement drive 61 for moving the compression member 59 in a direction of compressing the subject and in a direction opposite thereto, and a strut 63 for supporting the compression-unit movement drive 61.

As shown in FIG. 4, the compression unit movement drive 61 includes a compressing operation drive motor 65, a reduction gear 67, a driving pulley 69, an idler pulley 71, a chain belt 73, and an arm 75. The compressing operation drive motor 65 has an output shaft that rotates forward and backward. The driving pulley 69 is attached to the output shaft of the pressure operation drive motor 65 via the reduction gear 67. The idler pulley 71 is rotatably attached to a position in a vertical direction relative to the driving pulley 69. The chain belt 73 for transferring power is attached to the driving pulley 69 and the idler pulley 71. The compression member 59 is attached to the chain belt 73 via the arm 75. Thereby, the compression member 59 moves upward and downward by power of forward and backward rotation transferred from the pressure operation drive motor 65 to the reduction gear 67, the driving pulley 69, and the chain belt 73, in this order.

Moreover, as shown in FIG. 3, the compression unit 3 is movably supported on the radiographing table 2 via the compression-unit supporting mechanism 77. The compression-unit supporting mechanism 77 is supported on the radiographing table 2 so as to move in the surface parallel to the surface 21a of the top board 21 on which the subject M is placed.

The compression-unit supporting mechanism 77 includes a third slide rail 79, a fourth slide rail 81, a third support block 83, and a fourth support block 85. Specifically, the third slide rail 79 is provided on an external side surface of the radiographing table 2 in the transverse direction (the Y-direction) in parallel with the long direction of the top board 21 (the X-direction). The third support block 83 is movably supported along the third slide rail 79. The fourth slide rail 81 is provided on the third support block 83 in parallel with the transverse direction of the top board 21 (the Y-direction). The fourth support block 85 is movably supported along the fourth slide rail 81. The compression unit 3 is supported on the fourth support block 85.

A first brake 87 is provided on the third support block 83. The first brake 87 locks the compression unit 3 that is supported as to move in the longitudinal direction of the top board 21 of the radiographing table 2. A second brake 89 is provided on the fourth support block 85. The second brake 89 locks the compression unit 3 that is supported as to move in the transverse direction of the top board 21 of the radiographing table 2. That is, the compression unit 3 is locked in a given position, e.g., a retracted position, by the first brake 87 and the second brake 89.

Reference is now made to FIG. 1. A compression unit drive controller 91 controls compressing of the compression member 59 against a site of interest of the subject M and locking of the compression unit 3 into a given position through actuating the first brake 87 and the second brake 89.

<Connection of FPD and Compression Unit>

Reference is now made to FIG. 3. The X-ray apparatus 1 includes a connecting part 93 for selectively connects and disconnects the FPD 23 to and from the unit 3. Specifically, the connecting part 93 has connecting parts 93a and 93b on an FPD 23 side and a compression unit 3 side, respectively. The connecting part 93a is placed on a side surface of the second support block 35 on the compression unit 3 side for supporting the FPD 23. The connecting part 93b is placed on a fourth support block 85 for supporting the compression unit 3. The connecting part 93 is formed of an electronic lock that performs connection via a pin or a hook. The compression unit 3 is connected to the FPD 23 via the fourth support block 85 of the compression unit supporting mechanism 77.

Reference is now made to FIG. 5. When seen the FPD 23 and the compression unit 3 connected via the connecting part 93 from a perpendicular direction relative to the surface 21a of the top board 21, they are formed such that the center of the compression member 59 of the compression unit 3 conforms to the center of the detecting surface of the FPD 23. As a result, the compression member 59 of the compression unit 3 can always press a site of interest of the subject M at the center of the detecting surface of the FPD 23. Here, the X-ray tube movement controller 19 and the radiographing table drive controller 57 control the X-ray tube 5 and the FPD 23 in position such that the center of an X-ray beam applied from the X-ray tube 5 (the center of an irradiation field) conforms to the center of the detecting surface of the FPD 23. Consequently, the center of the compression member 59 of the compression unit 3 can conforms to the center of the X-ray beam applied from the X-ray tube 5.

The FPD 23 and the compression unit 3 connected via the connecting part 93 can be moved integrally into a given position in a plane parallel to the surface 21a of the top board 21. So, the X-ray detector movement drive 27 of the radiographing table 2 can move not only the FPD 23 but also the compression unit 3.

Reference is now made to FIG. 1. A connection controller 95 controls the connecting part 93 so as to connect the FPD 23 to the compression unit 3 or so as to disconnect the FPD 23 from the compression unit 3.

Moreover, the X-ray apparatus includes a main controller 97 for performing an overall control of the X-ray irradiation controller 17, the radiographing table drive controller 57, the compression-unit drive controller 91, the connection controller 95, and an image processor (107) to be mentioned later. The X-ray apparatus also includes an input unit 99, a memory 101, and a display 103. The input unit 99 inputs information needed for operation of the X-ray supporting device 1, the radiographing table 2, and the compression unit 3, and performs the operation. The memory 101 stores inputted information and X-ray images. The display unit 103 displays X-ray images. Moreover, the X-ray apparatus includes an A/D converter 105 for conversion into digital signals, and an image processor 107 for performing given image processing to the X-ray image having converted into the digital signals. The signals of intensity distribution of X-rays applied from the X-ray tube 5 through the subject M and detected by the FPD 23 are sent to the A/D converter 105, the image processor 107, in this order, and an X-ray image is displayed by the display unit 103.

Figure 6:
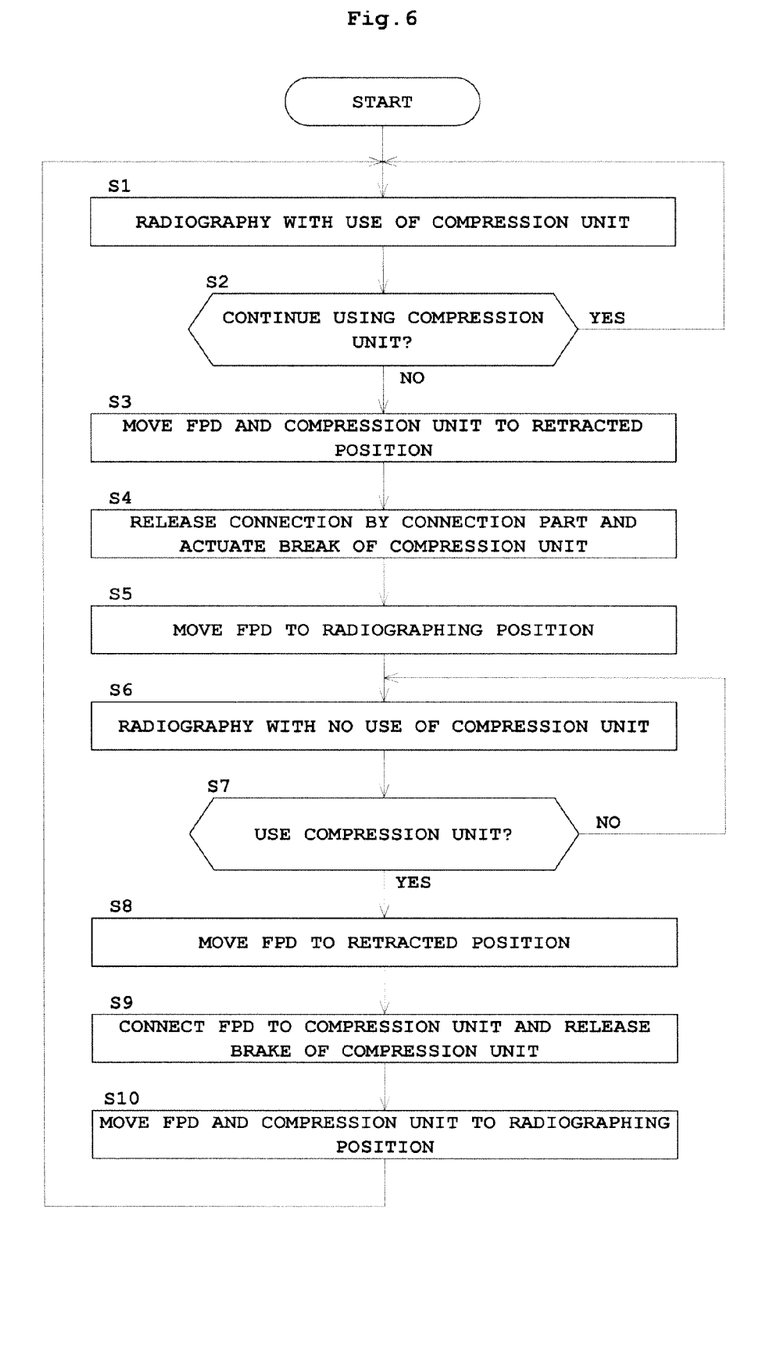
FIG. 6 is a flow chart for illustrating operations of the X-ray apparatus according to the example.

Next, description will be given of operations of the X-ray apparatus with reference to drawings. Especially, operation of the FPD 23 and the compression unit 3 is to be described with and without use of the compression unit 3 upon radiography. FIG. 6 is a flow chart for illustrating operations of the X-ray apparatus.

[Step S1] Radiography is performed with use of the compression unit 3. Herein, the FPD 23 and the compression unit 3 are connected via the connecting part 93. Consequently, the compression unit 3 moves as the FPD 23 moves. Moreover, the center of the detecting surface of the FPD 23 conforms to the center of the compression member 59 of the compression unit 3. As a result, an X-ray image can be acquired while compressing operation is always performed at the center of the detecting surface of the FPD 23.

[Step S2] The process returns to Step S1 where radiography continues with use of the compression unit 3. The process proceeds to Step S2 where radiography is performed with no use of the compression unit 3.

[Step S3] The compression unit 3 is moved into the retracted position out of the way, indicated by the numeral S in FIGS. 2 and 5, set in advance. The compression unit 3 is moved into the retracted position while the FPD 23 and the compression unit 3 are connected integrally via the connecting part 93. The FPD 23 and the compression unit 3 connected via the connecting part 93 are moved by the X-ray detector movement drive 27 for the FPD23. The compression member 59 and the arm 75 are housed into a storage space of the compression unit movement drive 61 upon the movement into the retracted position.

[Step S4] The FPD 23 and the compression unit 3 connected integrally via the connecting part 93 are moved into the retracted position, and then the FPD 23 is disconnected from the compression unit 3 by the connecting part 93. While disconnection by the connecting part 93 is performed, the first brake 87 and the second brake 89 of the compression unit 3 operate to lock the compression unit 3 in the retracted position. As for the timing of releasing connection of the connecting part 93 and operation of the brakes of the compression unit 3, connection of the connecting part 93 may be released approximately simultaneously with operation of the first brake 87 and the second brake 89 of the compression unit 3. Alternatively, connection of the connecting part 93 may be released after operation of the first brake 87 and the second brake 89 of the compression unit 3.

[Step S5] The FPD 23 disconnected by the connecting part 93 is moved by the X-ray detector movement drive 27 independently of the compression unit 3 into a radiographing position, i.e. the center of the X-ray beam applied from the X-ray tube 5.

[Step S6] After the FPD 23 is moved into the radiographing position, radiography with no use of the compression unit 3 is conducted. Herein, since the compression unit 3 is locked in the retracted position, a space can be made around the subject M placed on the top board 21 of the radiographing table 2.

[Step S7] After the radiography with no use of the compression unit 3 is conducted, the process proceeds to the next step S8 when radiography with use of the compression unit 3 is conducted. The process returns to Step S6 when the radiography with no use of the compression unit 3 continues.

[Step S8] When radiography with use of the compression unit 3 is conducted, the FPD 23 is moved again by the X-ray detector movement drive 27 into the retracted position where the compression unit 3 is locked.

[Step S9] The FPD 23 and the compression unit 3 are connected via the connecting part 93. The connecting part 93 performs connection through contacting the connecting part 93a of the FPD 23 to the connecting part 93b of the locked compression unit 3. The connecting part 93 connects the FPD 23 to the compression unit 3, and the first brake 87 and the second brake 89 of the compression unit 3 are released. The connecting part 93 may perform connection approximately simultaneously with releasing lock of the first brake 87 and the second brake 89 of the compression unit 3. The connecting part 93 may perform connection before releasing lock of the first brake 87 and the second brake 89 of the compression unit 3.

[Step S10] The compression unit 3 in the retracted position and the FPD 23 are connected via the connecting portion 93, and then the connected compression unit 3 and the FPD 23 are moved into a radiographing position by the X-ray detector movement drive 27. The process returns to Step S1.

With the X-ray apparatus having the foregoing configuration, the compression unit 3 is movably supported on the radiographing table 2 via the compression unit supporting mechanism 77. As a result, the compression unit 3 can move independently of the X-ray tube supporting device 1 and the FPD 23. The X-ray apparatus also includes the connecting part 93 for connecting and disconnecting the FPD 23 to and from the compression unit 3. Consequently, when the compression unit 3 is not used, the connecting part 93 disconnects the FPD 23 from the compression unit 3. Thereby the FPD 23 can be located in the radiographing position, whereas the compression unit 3 can be located in the retracted position out of the way of an operator OP. As a result, a space is generated around the subject M placed on the top board 21 of the radiographing table 2, which achieves access to the subject M from the space or arrangement of devices MA such as a monitor of an endoscope and an electrocardiogram in the space. On the other hand, when the compression unit 3 is used, the connection part 93 connects the FPD 23 to the compression unit 3. Thereby the center of the compression member 59 of the compression unit 3 can conform to the center of the detecting surface of the FPD 23. So, the compression member 59 of the compression unit 3 can always press a site of interest of the subject M at the center of the detecting surface of the FPD 23. As a result, the compression unit 3 can be operated with more ease rather than the configuration in which the FPD 23 and the compression unit 3 align individually.

Moreover, the radiographing table 2 includes an X-ray detector movement drive 27 for driving the FPD 23 as to move in a plane parallel to the surface 21a of the top board 21 on which the subject M is placed. Thereby X-ray detector movement drive 27 can not only move the FPD 23 into a given position, but also move the FPD 23 and the compression unit 3 integrally that are connected via the connection part 93. That is, the X-ray detector movement drive 27 for moving the FPD 23 can move the compression unit 3. Consequently, the foregoing configuration can achieve a simple configuration and thus can suppress manufacturing costs rather than a configuration in which an actuator other than the X-ray detector movement drive 27 is provided for moving the compression unit 3.

Figure 7:
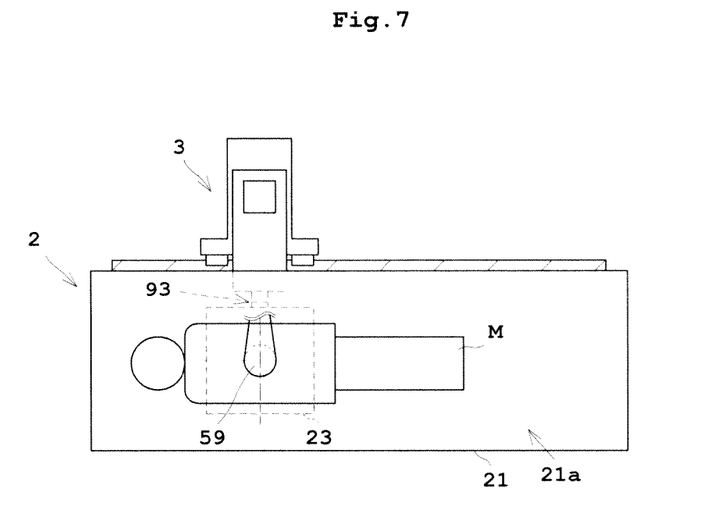
FIG. 7 is a view for explanation of effects of the X-ray apparatus according to the example in which a compression unit is used.
Figure 8:
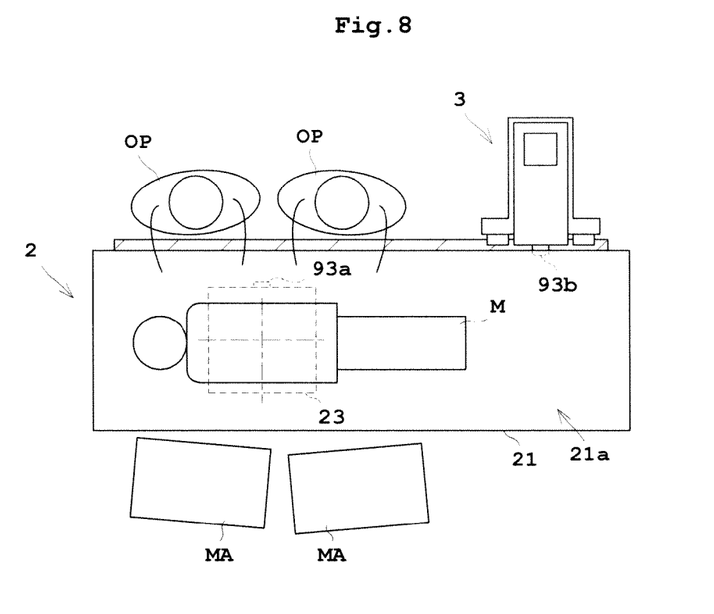
FIG. 8 is a view for explanation of effects of the X-ray apparatus according to the example in which a compression unit is not used.

Next, referring is made to FIGS. 7 and 8. FIG. 7 shows the case where radiography is conducted with use of the compression unit 3, whereas FIG. 8 shows the case where radiography, etc. is conducted with no use of the compression unit 3. As shown in FIG. 7, when radiography is conducted with use of the compression unit 3, the connection part 93 connects the FPD 3 to the compression unit 3. Consequently, the center of the detecting surface of the FPD 23 can conform to the center of the compression member 59 of the compression unit 3 for compressing the subject M. Thereby compressing can always be made at the center of the detecting surface of the FPD 23. When radiography is conducted with no use of the compression unit 3, the FPD 23 and the compression unit 3 integrally move, and accordingly a range of access to the subject M is restricted upon radiography while the subject M is inspected with an endoscope. Thus, as shown in FIG. 8, the FPD 23 and the compression unit 3 connected via the connecting part 93 are moved into the retracted position, and then the connecting part 93 disconnects them, thereby only the FPD 23 can be moved independently. On the other hand, the compression unit 3 is in the retracted position out of the way. As a result, a space is generated around the subject M placed on the surface 21a of the top board 21 of the radiographing table 2, which enables an operator OP to make access to the subject M from the space or to arrange devices MA such as a monitor of an endoscope and an electrocardiogram in the space.

Example 2

Figure 9:
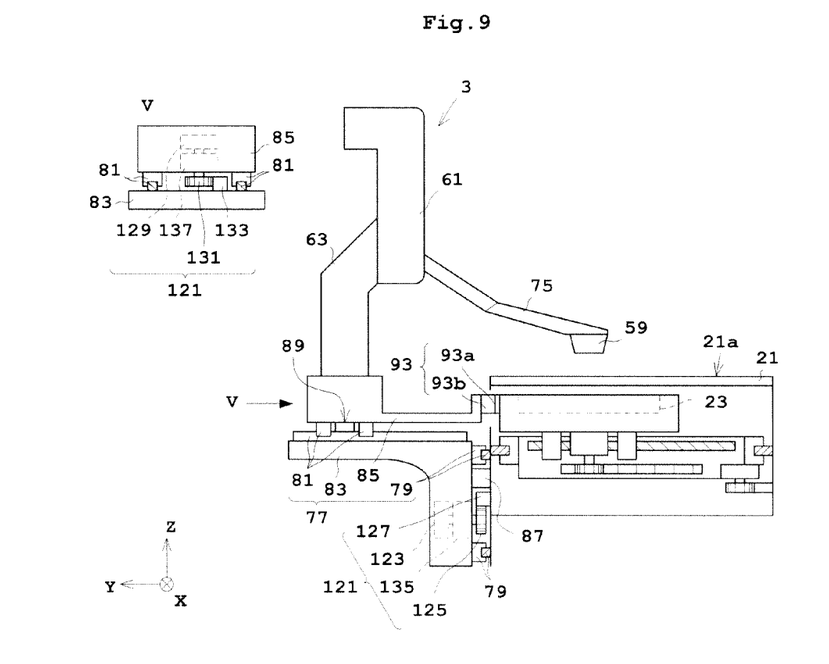
FIG. 9 is a schematic left side view of a compression unit and a radiographing table of an X-ray apparatus according to another example.

Next, Example 2 of this invention will be described with reference to the drawings. FIG. 9 is a schematic left side view of a radiographing table 2 and a compression unit 3 of an X-ray apparatus according to Example 2. Explanation on the configuration common to that of Example 1 is to be omitted.

In Example 1, the FPD 23 is connected to the compression unit 3 via the connecting part 93, and then the X-ray detector movement drive 27 for moving the FPD 23 moves the compression unit 3 and the FPD 23 integrated with each other. This configuration, however, is not limitative. In addition to the X-ray detector movement drive 27, a compression-unit movement drive 121 may be provided for driving and moving the compression unit 3 movably supported.

The X-ray apparatus includes a compression-unit movement drive 121 for driving the compression unit 3 as to move in a plane parallel to a surface 21a of the top board 21 on which the subject M is placed. The compression-unit movement drive 121 includes a third motor 123, a third pinion 125, and a third rack 127 for driving the compression unit 3 as to move in the longitudinal direction of the surface 21a of the top board 21. The compression-unit movement drive 121 also includes a fourth motor 129, a fourth pinion 131, and a fourth rack 133 for driving the compression unit 3 as to move in the transverse direction of the surface 21a of the top board 21.

The compression-unit movement drive 121 also includes a first clutch 135 and a second clutch 137 for selectively transferring and interrupting power to move and actuate the compression unit 3. The compression unit movement drive 121 is provided with a rotary encoder, not shown, as a position detection sensor, for example.

The third rack 127 is provided on the external side surface of the radiographing table 2, i.e., the main frame 37, in parallel with the longitudinal direction of the top board 21 (the X-direction). The third pinion 125 is attached to an output shaft of the third motor 123 via the first clutch 135. The third motor 123 is attached to the third support block 83 such that teeth of the third rack 123 engage with teeth of the third pinion 125. Thereby, the compression unit 3 can be moved in the longitudinal direction of the surface 21a of the top board 21 (the X-direction).

Moreover, the fourth rack 133 is provided on the third block 83 in parallel with the transverse direction of the top board 21 (the Y-direction). The fourth pinion 131 is attached to an output shaft of the fourth motor 129 via the second clutch 137. The fourth motor 129 is attached to the fourth support block 85 such that teeth of the fourth rack 133 engage with teeth of the fourth pinion 131. Thereby, the compression unit 3 can be moved in the transverse direction of the surface 21a of the top board 21 (the Y-direction).

The first clutch 135 and the second clutch 137 provide transfer and intercept of power from the third motor 123 and the fourth motor 129, respectively. For instance, when the first clutch 135 and the second clutch 137 are set in an intercepted state, the FPD 23 and the compression unit 3 connected via the connecting part 93 can be moved only by the X-ray detector movement drive 27. Thereby the X-ray detector movement drive 27 can move the FPD 23 and the compression unit 3 with no load by the third motor 123 and the fourth motor 129.

When the compression unit 3 is used, the connection part 93 connects the FPD 23 to the compression unit 3. The first clutch 135 and the second clutch 137 are set to an intercepted state such that power is not transferred from the third motor 123 and the fourth motor 129. On the other hand, when the compression unit 3 is not used, the connection part 93 disconnects the FPD 23 from the compression unit 3 integrated therewith. Herein, the first clutch 135 and the second clutch 137 are in a state of transferring power from the third motor 123 and the fourth motor 129.

The connection part 93 performs connection at a connecting position, for example, set in advance. Alternatively, the connection part 93 performs connection such that the compression unit 3 is moved to the FPD 23. The compression unit drive controller 91 controls movement of the compression unit 3 by the compression unit movement drive 121.

As shown in FIG. 9, the first clutch 135 and the second clutch 137 are provided between the third motor 123 and the third pinion 125 and between the fourth motor 129 and the fourth pinion 131, respectively. However, this configuration is not limitative. For instance, the first clutch 135 and the second clutch 137 may be formed such that transfer and interception of power is performed between the third pinion 125 and the third rack 127 and between the fourth pinion 131 and the fourth rack 133, respectively. That is, it is only needed to transfer and intercept power from the third motor 123 and the fourth motor 129.

The X-ray apparatus of Example 2 with the foregoing configuration includes the compression-unit movement drive 121 for driving the compression unit 3 as to move. Consequently, when the compression unit 3 is not used, the compression-unit movement drive 121 can move the compression unit 3 independently of movement of the FPD 23. As a result, when the connecting part 93 disconnects the FPD 23 from the compression unit 3, the compression unit 3 can be located in the retracted position by the compression-unit movement drive 121. The FPD 23 can perform operation for radiography immediately. In other words, the foregoing configuration can enhance working efficiency rather than the configuration in which the FPD 23 and the compression unit 3 integrally connected are moved into the retracted position by the X-ray detector movement drive 27 and only the FPD 23 is moved into the radiographing position after disconnection of the connecting part 93.

This invention is not limited to the foregoing embodiment, but may be modified as follows.

(1) In the foregoing examples, the X-ray tube supporting device is of ceiling-suspended travelling type suspended from the ceiling, but is not limited to this. It may be an X-ray tube supporting device of floor travelling type.

(2) In the foregoing examples, the X-ray detector is a flat panel X-ray detector (FPD), but is not limited to this. It may include an image intensifier (I.I.).

In this case, the X-ray detector supporting mechanism 25 supports an image intensifier appropriately.

(3) In each of the foregoing examples, the X-ray detector movement drive 27 and the compression unit movement drive 121 each include a motor, a pinion, and a rack. However, they are not limited to this configuration. For instance, the X-ray detector movement drive 27 and the compression unit movement drive 121 may include a drive pulley, an idler pulley, and a belt.

The invention claimed is:
1. An X-ray apparatus comprising:
an X-ray tube supporting device with an X-ray tube for applying X-rays;

a radiographing table with a top board for supporting a subject placed thereon and an X-ray detector facing the X-ray tube across the top board for detecting X-rays transmitting through the subject, the X-ray detector being movable in a longitudinal direction of the top board;

a compression unit, movable in the longitudinal direction of the top board independently from both the X-ray tube supporting device and the X-ray detector, for compressing a site of interest of the subject; and a connecting part for connecting the X-ray detector to the compression unit and disconnecting the X-ray detector from the compression unit.

2. The X-ray apparatus according to claim 1, wherein the radiographing table comprises an X-ray detector movement drive for driving the X-ray detector as to move in a plane parallel to a surface of the top board on which the subject is placed.

3. The X-ray apparatus according to claim 2, wherein the compression unit is movably supported on the radiographing table.

4. The X-ray apparatus according to claim 3, wherein the X-ray tube supporting device is ceiling-suspended.

5. The X-ray apparatus according to claim 4, further comprising a compression-unit movement drive for driving the compression unit as to move in a plane parallel to a surface of the top board on which the subject is placed.

6. The X-ray apparatus according to claim 3, further comprising a compression-unit movement drive for driving the compression unit as to move in a plane parallel to a surface of the top board on which the subject is placed.

7. The X-ray apparatus according to claim 2, wherein the X-ray tube supporting device is ceiling-suspended.

8. The X-ray apparatus according to claim 7, further comprising a compression-unit movement drive for driving the compression unit as to move in a plane parallel to a surface of the top board on which the subject is placed.

9. The X-ray apparatus according to claim 2, further comprising a compression-unit movement drive for driving the compression unit as to move in a plane parallel to a surface of the top board on which the subject is placed.

10. The X-ray apparatus according to claim 1, wherein the compression unit is movably supported on the radiographing table.

11. The X-ray apparatus according to claim 10, wherein the X-ray tube supporting device is ceiling-suspended.

12. The X-ray apparatus according to claim 11, further comprising a compression-unit movement drive for driving the compression unit as to move in a plane parallel to a surface of the top board on which the subject is placed.

13. The X-ray apparatus according to claim 10, further comprising a compression-unit movement drive for driving the compression unit as to move in a plane parallel to a surface of the top board on which the subject is placed.

14. The X-ray apparatus according to claim 1, wherein the X-ray tube supporting device is ceiling-suspended.

15. The X-ray apparatus according to claim 14, further comprising a compression-unit movement drive for driving the compression unit as to move in a plane parallel to a surface of the top board on which the subject is placed.

16. The X-ray apparatus according to claim 1, further comprising a compression-unit movement drive for driving the compression unit as to move in a plane parallel to a surface of the top board on which the subject is placed.

* * * * *